United States Patent [19]

Karapasha et al.

[11] Patent Number: 5,306,487
[45] Date of Patent: Apr. 26, 1994

[54] HIGH CAPACITY ODOR CONTROLLING COMPOSITIONS

[76] Inventors: Nancy Karapasha; Theresa L. Johnson, both of P.O. Box 398707, Cincinnati, Ohio 45239-8707

[21] Appl. No.: 908,588

[22] Filed: Jun. 29, 1992

Related U.S. Application Data

[63] Continuation of Ser. No. 478,801, Feb. 12, 1990, abandoned.

[51] Int. Cl.$^5$ .............................................. A61L 15/16
[52] U.S. Cl. .................. 424/76.6; 424/78.1; 604/359
[58] Field of Search ............ 424/76.3, 76.4, 76.5, 424/76.6, 404, 443, 78.1, 489, 501; 604/359

[56] References Cited

U.S. PATENT DOCUMENTS

| | | | |
|---|---|---|---|
| 2,690,415 | 8/1954 | Shuler | 167/84 |
| 2,933,455 | 4/1960 | Poying | 252/428 |
| 3,093,546 | 6/1963 | Atkinson | 128/290 |
| 3,340,875 | 9/1967 | Dudley et al. | 128/290 |
| 3,804,094 | 4/1974 | Manoussos et al. | 128/290 R |
| 3,939,838 | 2/1976 | Fujinami et al. | 128/290 R |
| 4,009,684 | 3/1977 | Kliment et al. | 424/76.3 |
| 4,385,632 | 5/1983 | Odelhög | 605/360 |
| 4,525,410 | 6/1985 | Hagiwara et al. | 428/198 |
| 4,547,195 | 10/1985 | Jackson | 604/359 |
| 4,654,039 | 3/1987 | Brandt et al. | 604/368 |
| 4,795,482 | 1/1989 | Gioffre et al. | 55/75 |
| 4,826,497 | 5/1989 | Marcus et al. | 604/359 |
| 4,963,431 | 10/1990 | Goldskin et al. | 428/290 |

FOREIGN PATENT DOCUMENTS

| | | |
|---|---|---|
| 815446 | 9/1974 | Belgium . |
| 0304952 | 3/1989 | European Pat. Off. . |
| 3816352.7 | 11/1989 | Fed. Rep. of Germany . |
| 54-141857 | 11/1979 | Japan . |
| 63-224734A | 9/1988 | Japan . |
| 63-242261A | 10/1988 | Japan . |
| PCT/US80/-01662 | 6/1981 | PCT Int'l Appl. . |

OTHER PUBLICATIONS

Abscents-A New Approach for Odor Control (A. J. Gioffre)-Union Carbide brochure.

Primary Examiner—Thurman K. Page
Assistant Examiner—Amy Hulina
Attorney, Agent, or Firm—Jerry J. Yetter; Eric W. Guttag

[57] ABSTRACT

Compositions comprise absorbent gelling materials combined with high levels of odor-controlling agents by means of binders. The preferred particle form of the compositions is easy to handle, and is used in the manufacture of catamenials, diapers, bandages, and the like. The absorbent gelling material enhances the odor-controlling properties of the compositions by helping to control ammonia odors.

1 Claim, No Drawings

HIGH CAPACITY ODOR CONTROLLING COMPOSITIONS

This is a continuation of application Ser. No. 478,801, filed on Feb. 12, 1990 now abandoned.

TECHNICAL FIELD

The present invention relates to odor-controlling agents which are especially useful in articles such as catamenials, diapers, bandages, adult incontinence garments, and the like. The odor-controlling agents herein are designed to combat a broad spectrum of odoriferous materials, including sour "ammonia-type" odors. The preferred particulate form of the odor-controlling agents herein simplifies the manufacture of such articles, and the odor-controlling agents retain their activity throughout the manufacturing process.

BACKGROUND OF THE INVENTION

A wide variety of absorbent structures designed not only to be efficient for the absorption of body fluids such as blood, urine, menses, and the like, but also to be sanitary and comfortable in-use are known in the literature. Disposable products of this type generally comprise some sort of fluid-permeable topsheet material, an absorbent core, and a fluid-impermeable backsheet material. Various shapes, sizes and thicknesses of such articles have been explored in an attempt to make their use more comfortable and convenient.

One particular aspect of sanitary products which has been under investigation for many years is that of odor control. Many body fluids have an unpleasant odor, or develop such odors when in contact with air and/or bacteria for prolonged periods. The literature is replete with references relating to odor control in products such as diapers and catamenials.

Various odor-controlling agents have been disclosed in the literature. In particular, certain zeolitic materials are becoming known for their odor-controlling properties. Zeolitic materials are generally quite safe, and while they do effectively control many odors associated with body fluids, it has been determined that, unfortunately, they do not provide optimal control for ammonia odor and similar odors, presumably associated with short-chain amines and/or urea.

Moreover, the zeolitic odor-controlling materials tend to be in the form of very small, dusty particles which are difficult to handle on a commercial scale. Such materials tend to be blown or vacuumed up from absorbent structures moving at the high speeds (500–600 items/minute) used on modern catamenial or diaper manufacturing lines.

It has been suggested that particulate odor-controlling agents can be adhered to the surface of larger particles of absorbent gelling materials using moisture. The resulting particles are less dusty, easier to handle and exhibit improved control of odors, including ammonia. However, it has now been discovered that such particles can typically be "loaded" with only up to about 10% by weight of odor-controlling agent using water. Preferably, the mixed absorbent gelling material/odor-controlling agent particle would contain greater than such a modest loading, more conveniently, on the order of a 20% or greater loading of said particulate odor-controlling agent.

Finally, it has now been determined that certain particulate odor-controlling agents can lose a portion of their odor-controlling activity during the manufacture of catamenials, diapers and the like. While the reason for this loss is not entirely clear, it is conceivable that the agents adsorb vagrant materials from the manufacturing process and, thus, their odor-adsorbing capacity is partially "used up".

Accordingly, it would be desirable to provide odor-controlling agents which would control not only complex odors, such as those the zeolitic materials handle easily, but also simple odors, such as ammonia. It would also be desirable to provide such agents in a form which is easy to handle.

The present invention provides a means for safely and effectively overcoming these deficiencies by combining particulate odor-controlling agents with absorbent gelling materials, using binder materials, as disclosed more fully hereinafter. These and other advantages associated with the present invention will be seen from the disclosure, hereinafter.

BACKGROUND ART

The patent literature contains a considerable number of references relating to odor control in sanitary products such as diapers, bandages and catamenials. The following are illustrative.

EPO Patent Application 0304952 (published Mar. 1, 1989, U.S. priority Aug. 28, 1987), relates to a swellable polymer coated on a web or tissue, and with a deodorant powder, for use in fluid absorbent structures such as sanitary napkins.

U.S. Pat. No. 4,385,632 (May 31, 1983) by S. O. Odelhög, assigned to Landstingens Inköpscentral teaches copper odor control agents used on the surface of absorbent articles.

U.S. Pat. No. 3,804,094 (Apr. 16, 1974) by K. Dossou, M. Gascon, G. Manoussos, assigned to L'Oreal Fr teaches a periodic acid odor control agent used on the surface of an absorbent article.

U.S. Pat. No. 4,525,410 (Jun. 25, 1985) by Z. Hagiwara, H. Ohki, S. Hoshino, S. Nohara, S. Ida, K. Tagawa, assigned to Kanebo, Ltd. and Kanto Chemical Co., Inc. teaches zeolite particles (doped with bactericidal cations) assertedly stably held in a fibrous web by incorporating some portion of meltable fibers in the web, and applying heat; said to be useful as the "outside cover layer" in, e.g., "general sanitary goods".

Japanese J63224734-A (88.09.19) Priority 87JP-058738 (87.03.16) J63224734 ASK KK relates to a paper comprising a powder or fiber obtained by grinding sepiolite, said paper having deodorizing capacity.

Japanese J63242261-A (88.10.07) 87JP-076111 J63242261 ASK KK relates to an odor-absorbing mat with sepiolite powder, a nonwoven fabric layer, and what appears to be a sheet to which the sepiolite is attached by adhesive.

U.S. Pat. No. 2,690,415 (Sep. 28, 1954) by F. A. Shuler teaches particles of odor-absorbing materials uniformly affixed at the interstices of a permeable web by adhesive to provide an odor absorbent medium for, e.g., catamenials. Particulate carbon, silica gel and activated alumina are noted. Shifting/displacement of the particulates is assertedly avoided and the sheet is flexible.

U.S. Pat. No. 3,093,546 (Jun. 11, 1963) by R. L. Atkinson, teaches halogenated diphenyl methane derivatives "advantageously placed on the surface of a catamenial dressing" to "obtain prompt deodorizing activity".

Japanese J54141857 (J87019865) teaches the manufacture of powder (including zeolites) sheets by laminating the powder between a first and second sheet. Powders include activated carbon, zeolite, etc. The abstract indicates use in catamenials or deodorizing materials.

BE-815446 (Abstract) teaches sanitary towels with chlorophyll crystals or activated carbon, either in the absorbent layer, on the surface, or (per abstract) between.

ABSCENTS (odor-control molecular sieve from Union Carbide)—Use in diapers and catamenials is specifically noted in Union Carbide brochure (A. J. Gioffre 1988). The brochure indicates that UC's market research shows potential benefits in such products. U.S. Pat. Nos. 4,795,482 and 4,826,497, relate to ABSCENTS used as an odor-controlling agent, generally, and in sanitary products, in particular.

Various other patents relating to various absorbent gelling materials, topsheets, diaper and catamenial designs, and the like, are listed in the Detailed Description and Examples, hereinafter. All documents cited in this specification are incorporated herein by reference.

SUMMARY OF THE INVENTION

The present invention encompasses a composition of matter, comprising a cohesive mixture of an absorbent gelling material, a water-soluble or water-dispersible binder material and a water-insoluble odor-controlling agent. The odor-controlling agent typically comprises greater than 10% by weight of the final composition. (For purposes of clarity, the percentage loading of the odor-controlling agent, e.g., zeolite, is calculated on the total weight of the final particles.)

Typical compositions herein are those wherein the absorbent gelling material is selected from acrylate and starch-acrylate absorbent gelling materials. The absorbent gelling material can also comprise a cellulosic or saccharidic material.

The preferred binder materials herein comprise a member selected from the group consisting of hydroxypropyl celluloses, hydroxyethyl celluloses, hydroxymethyl celluloses, $C_1$-$C_3$ alkyl-substituted celluloses, maltodextrin, and mixtures thereof. The most preferred binder materials comprise the class of hydroxypropyl celluloses. Other binders useful herein include gelatins, gum acacia, starch derivatives, and the like, which are readily dispersible in water or body fluids.

Preferred particulate odor-controlling agents used herein comprise a member selected from the group consisting of intermediate $SiO_2/AlO_2$ zeolites, high $SiO_2/AlO_2$ zeolites, activated carbon, and mixtures thereof.

Typical compositions to this invention are in the form of particles having an average size, by sieve analysis, greater than about 100 microns. Preferably, such compositions comprise at least 20% by weight, more preferably at least 30%, of said odor-controlling agent.

Another useful composition herein comprises coated aggregates of the aforesaid zeolites (1–15 micron size), absorbent gelling material (typically 10–100 micron size) and binder, the overall size of the final aggregated particles being at least 50 microns (typically 100–750 microns). Such aggregated particles allow the manufacturer to conveniently use zeolites with absorbent gelling material "fines" in the manufacture of absorbent articles.

A preferred composition according to this invention comprises a cohesive mixture in the form of particles, said particles having a size, by sieve analysis, greater than about 200 microns, said particles comprising:
 (a) at least 20% (preferably at least 30%) by weight of a particulate odor-controlling agent selected from zeolite and activated carbon odor-controlling agents, and mixtures thereof;
 (b) at least 40% by weight of an absorbent gelling material; and
 (c) a water-soluble or water-dispersible binder material.

The invention also encompasses absorbent structures in the form of diapers, catamenials, or pantiliners comprising the aforesaid compositions.

Typically, such absorbent structures comprise a conventional water-permeable topsheet, a water-impermeable backsheet, and an absorbent core, said core comprising a cohesive mixture in the form of particles or aggregates, as noted above, said particles or aggregates having a size, by sieve analysis, preferably greater than about 200 microns, said particles comprising:
 (a) at least 20% (preferably at least 30%) by weight of a particulate odor-controlling agent selected from zeolite and activated carbon odor-controlling agents, and mixtures thereof;
 (b) at least 40% by weight of an absorbent gelling material; and
 (c) a water-soluble or water-dispersible binder material.

As is well-known, the core can also contain auxiliary fibrous absorbents such as wood pulp, and the like. The aforesaid particles can be dispersed throughout a matrix of said auxiliary absorbent, in known fashion.

The invention also encompasses a process for affixing particulate odor-controlling agents to particles of absorbent gelling materials, comprising contacting said absorbent gelling materials, comprising contacting said absorbent gelling materials, with said odor-controlling agents in the presence of a water-soluble or water-dispersible binder material, said process being carried out in the presence of water. In a convenient mode, the process is carried out in a fluidized bed apparatus.

All percentages, ranges and ratios herein are by weight, unless otherwise specified.

DETAILED DESCRIPTION

The compositions and methods for controlling odors in the manner of this invention involve the conjoint use of zeolitic-type materials and absorbent gelling materials ("AGM's"), as described more fully hereinafter.

The articles which employ said zeolitic/AGM odor-control technology disclosed herein can be prepared using constituents that are otherwise very well-known in current commercial practice, and reference can be made to the various patents mentioned herein and to the general sanitary products patent literature and trade catalogues for such items. Likewise, methods and apparatus for assembling disposable diapers, catamenials, bandages, and the like are known from patents and engineering literature.

While the constituents used in the assembly of catamenials, disposable diapers, and the like, are well-known, the following may be mentioned by way of example. It is to, be understood that the present invention resides in the novel assemblage of such items, or, their equivalents, into the odor-controlling, absorbent materials and structures disclosed herein, rather than in the constituents per se.

The articles which employ said zeolitic/AGM odor-control technology disclosed herein can be prepared using constituents that are otherwise very well-known in current commercial practice, and reference can be made to the various patents mentioned herein and to the general sanitary products patent literature and trade catalogues for such items. Such items typically comprise an absorbent "core" interposed between a "tqpsheet" and a "backsheet". Likewise, methods and apparatus for assembling disposable diapers, catamenials, bandages, and the like are known from patents and engineering literature.

While the, constituents used in the assembly of catamenials, disposable diapers, and the like, are well-known, the following may be mentioned by way of example. It is to be understood that the present invention resides in the novel assemblage- of such items, or their equivalents, into the odor-controlling absorbent materials and structures disclosed herein, rather than in the constituents per se.

I. Zeolite Odor-Controlling Agent—The manufacture of zeolite materials of the type used in the practice of this invention is well-known, and reference can be made to the voluminous literature for typical synthetic procedures.

In order to assist the formulator and user of the compositions, articles and methods of this invention (but not by way of limitation), attention is directed to the synthetic procedures described in the following reference texts: ZEOLITE SYNTHESIS, ACS Symposium Series 398, Eds: M. L. Occelli and H. E. Robson (1989) pages 2–7; ZEOLITE MOLECULAR SIEVES, Structure, Chemistry and Use, by D. W. Breck, John Wiley & Sons (1974) pages 245-250, 313-314 and 348-352; MODERN APPLICATIONS OF MOLECULAR SIEVE ZEOLITES, Ph.D. Dissertation of S. M. Kuznicki, U. of Utah (1980), available from University Microfilms International, Ann Arbor, Michigan, pages 2–8.

It is to be understood that the zeolites used herein are not of the fibrous type, e.g., various Mordenites and some type Y zeolites, since these may cause asbestos-type safety issues. Accordingly, the term "zeolite" as used here-in is intended to encompass only the nonfibrous zeolites. Moreover, it is preferred that the zeolites used herein be substantially hydrophobic, since they generally must function to adsorb odors in the presence of body fluids when used in the articles and processes disclosed herein. While some naturally-occurring zeolites meet the objectives of this invention, the synthetic zeolites of the types available in commerce are generally more preferred.

In general terms, traditional zeolites comprise an aluminate/silicate framework, with associated cations, M, providing overall electrical neutrality. Empirically, the zeolite framework can be represented as

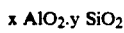
x $AlO_2$.y $SiO_2$ and the electrical neutral zeolite as

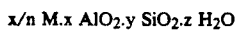
x/n M.x $AlO_2$.y $SiO_2$.z $H_2O$ wherein: x and y are each integers, M is a cation and n is the charge on the cation. As noted by the empirical formula, zeolites may also comprise waters of hydration (z $H_2O$)- Reference to the literature will illustrate that M can be a wide variety of cations, e.g., $Na^+$, $K^+$, $NH_4^+$, alkylammonium, heavy metals and the like. The practice of the present invention does not require any particular selection of cation; accordingly, sodium ion is convenient and preferred.

It is to be understood that a first class of preferred zeolites used herein has entirely different ratios Of $SiO_2/AlO_2$ than the zeolites disclosed in U.S. Pat. Nos. 4,795,482 and 4,826,497. Stated otherwise, the ratio of integers x and y in this first class of zeolites is such that the zeolites are typically characterized as "intermediate" silicate/aluminate zeolites, whereas those of U.S. Pat. Nos. 4,795,482 and 4,826,497 are "high" silicate/aluminate zeolites.

While not intending to be limited by theory, it appears that the silicate/aluminate ratios of the "intermediate" zeolites used in the practice of this invention result in several advantages over the "high" zeolites. First, the intermediate zeolites have a higher capacity for amine-type odors than the high zeolites. This is important to controlling urine and menses odors. Second, the intermediate zeolites have a larger surface area (700–800 $m^2/g$) than the high zeolites (ca. 400 $m^2/g$). This results in more efficient odor adsorptivity, on a wt./wt. basis; or, in the alternative, allows less zeolite to be used to adsorb a given amount of odor. Third, the intermediate zeolites appear to be somewhat more tolerant to moisture, and retain more of their odor-adsorbing capacity in the presence of water.

The "intermediate" zeolites used in this invention are characterized by $SiO_2/AlO_2$ molar ratios of less than about 10. Typically, the molar ratio of $SiO_2/AlO_2$ will range from about 2 to about 10.

The synthesis of intermediate zeolites forms no part of the present invention since various syntheses are known in the extensive zeolite literature. The following is given simply by way of illustration, and not limitation, of a synthetic procedure.

While different starting materials can yield zeolites, the same zeolite can be made from different reactants. Some reactant variables influencing the structure and composition of the final zeolite are:

the identity, ratio and order of addition of the reactants;
the strength of the base;
the temperature (ambient to ca. 100° C.);
mechanical agitation such as stirring; and
the gelation time (1 hour to days).

Once the desired gelation is achieved, the gel is transferred to a teflon or stainless steel container and placed in an autoclave. Crystal formation begins as the gel is subjected to constant or variable temperature at autogeneous pressure for an indefinite time. There are basically 3 recognized phases during transformation of the gel to crystals. The phases are (1) induction or nucleation (first crystal appears); (2) crystal growth; and (3) phase transformation. Some factors influencing the rate at which crystals form and grow are the temperature, pH, addition of seed crystals or templating materials for structure directing, stirring and centrifugation.

After phase transformation, the slurry is removed from the autoclave and filtered. The crystals are washed and dried at ca. 100° C. Further modifications are possible if so desired.

Post-Synthesis Modifications

Some post-synthesis modifications are a means of obtaining other traditional zeolites. For instance, counter ions can be exchanged such as:

Na-zeolite + NH₄Cl → NH₄-zeolite or

Na-zeolite + HCl → H-zeolite imparting unique adsorptive forces and modifying the pore size of, for example, an A, X or Y zeolite. Additionally, stabilization of traditional zeolites is possible. For example, a typical method of synthesizing an ultra-stable zeolite Y (USY) such as "VALFOR CP300-56" is as follows:

NaY + NH₄⁺ or NH⁺ exchange → NH₄NaY + calcine (650–800° C.) → USY

Synthesis of Special Zeolites

Several post-synthesis modification methods exist for making special zeolites. The methods include (1) pore modification; (2) surface modification; and (3) structural change. The first two methods consist of adsorbing species by chemical vapor deposition inside or on the zeolite. Pore modifiers such as SiH₄ and BH₃ and surface modifiers such as Si(OCH₄)₄, SiCl₄, TiCl₄ and SeCl₄ have been used to impart new unique properties to the zeolite. The most frequently used structural change method is to remove alumina from the main framework (i.e., de-aluminate). De-alumination can be performed by one of several routes such as (1) acid leaching; (2) steam (700°–900° C.); or (3) treatment with SiCl₄ at cold temperatures. An example of de-alumination is:

Zeolite Y + H₄EDTA → de-aluminated Zeolite Y

The following references further illustrate the synthesis of intermediate zeolites of the type employed herein: Lok, B. M., Cannan, T. R., and Messina, C. A., "The Role of Organic Molecules in Molecular Sieve Synthesis" Zeolites 3, 282-291 (1983); Barrer, R. M. "Zeolites and Their Synthesis" Zeolites 1, 130-140 (1981); ZEOLITES FOR THE NINETIES, Proceedings of the 8th International Zeolite Conference, Eds. P. A. Jacobs and R. A. van Santen (1989) pages 119-372; and MOLECULAR SIEVES, Adv. Chem. Ser. 121, Eds. W. M. Meier and J. B. Uytterhoeven (1973).

A wide variety of intermediate zeolites suitable for use herein are commercially available from commercial suppliers such as Philadelphia Quartz and Conteka. Such materials are sold under various commercial and trade names such as VALFOR CP 301-68, VALFOR 300-63, VALFOR CP300-35 and VALFOR 300-56, from Philadelphia Quartz, and the CBV 100 series (other than Mordenite, as noted above) of zeolites from Conteka.

A second type of odor-controlling agent which can be employed in the practice of this invention comprises the "high ratio" zeolites. Such materials include, for example, the well-known "molecular sieve" zeolites of the ZSM, beta zeolite, etc., type (generally in the 1-10 micron particle size range) and the zeolite materials marketed under the trade name ABSCENTS by the Union Carbide Corporation and UOP, and which are typically available as a white powder in the 3-5 micron particle size range (see: ABSCENTS, A New Approach for Odor Control by A. J. Gioffre, copyright 1988 by the Union Carbide Corporation). Such materials are preferred over the "intermediate" zeolites when control of odors associated with sulfur compounds, e.g., thiols, mercaptans, as well as some control of amine odors, is desired.

The use of zeolites of the ABSCENTS type to control odors is fully described in U.S. Pat. No. 4,795,482, Jan. 3, 1989, to Gioffre and Marcus. In general, these molecular sieve odor-controlling agents appear to function by entrapping by chemical adsorption odoriferous substances within their molecular lattice structures. Whatever their mode of action, these odor-controlling agents can be characterized by their physical parameters, as follows. These agents are reported by Gioffre and Marcus to be crystalline siliceous molecular sieves in which at least about 90, and preferably at least about 95, percent of the framework tetrahedral oxide units are $SiO_2$ tetrahedra and which have a sorptive capacity for water at 25° C. and 4.6 of less than 10 weight percent. In the case of aluminosilicate molecular sieves, those "high ratio" zeolite odor-controlling agents have a framework $SiO_2/AlO_2$ molar ratio of from about 35 to infinity, and preferably from 200 to 500. Such siliceous molecular sieves have a pore diameter of at least 5.5 Angstroms, preferably at least 6.2 Angstroms. Preferably the adsorption capacity for water vapor at 25° C. and a water vapor pressure ($p/p_0$) of 4.6 is less than 6 weight percent. As stated by Gioffre and Marcus, the efficacy of these molecular sieves is not dependent on the presence of the water of hydration in the internal cavities of the microporous structure as a result of their hydrothermal formation. In fact, at least a major proportion, usually substantially all, of this original water of hydration is removed in the process of removing any pore-blocking templating agent which may be present in the adsorbent. Calcination effectively removes any organic moieties. Also, water washing, leaching or washing with a caustic or dilute mineral acid solution is advantageously utilized to remove extraneous synthesis reactants from the pore system. Lowering of the alkali metal content, particularly the nonzeolitic, i.e., occluded alkali metal compounds can also be beneficial. These procedures also serve to remove the original water of hydration.

As further disclosed by Gioffre and Marcus, such siliceous molecular sieves include the microporous crystalline aluminosilicates, i.e., the zeolitic molecular sieves as well as the so-called silica polymorphs. With respect to the latter compositions, their crystal lattices are ideally formed entirely of $SiO_2$ tetrahedral units, but the as-synthesized forms commonly contain at least trace amounts of aluminum derived from aluminum impurities in the synthesis reagents. The aluminosilicate molecular sieves comprise the large class of well-known crystalline zeolites. These high-silica molecular sieves are either commercially available or are prepared by methods well-known in the art, involving direct hydrothermal synthesis or involving certain types of crystal lattice dealuminations. A comprehensive review article by E. M. Flanigen concerning both "high" Si/Al zeolites and silica molecular sieves is published in "Proc. 5th Int. Conf. Zeolites, Naples, 1980", L. V. C. Rees, ed., Heyden, London, pp. 760-780. It is to be understood that all such materials are referred to herein simply as "zeolites", for convenience.

With respect to the foregoing ABSCENTS odor-controlling agents, it is important that their pore system be open so that the internal cavities of the crystals be accessible to the odor molecules. In the case of the aluminosilicates or silica polymorphs produced using large organic templating ions such as tetraalkylammonium ions, it is necessary to remove charge balancing organic ions and any occluded templating material in order to permit adsorption of the odor molecules. In such a removal process and also in the removal of inorganic debris, the original water of hydration is also removed. Upon exposure to the atmosphere, a portion of the water of hydration is reacquired, but this does not affect the characteristics of the molecular sieves which are preferred for the practice of the present invention, i.e., the molecular sieves can be employed in either a hydrated or dehydrated state, but, in general, the dehydrated state is preferred. In the case of most of the dealumination procedures referred to above, the original water of dehydration is also removed, and can similarly be replaced, if desired, for the practice of the invention.

More specifically, Gioffre and Marcus disclose that the class of their disclosed medium to large pore siliceous molecular sieves, from which the original, as-synthesized water of hydration has been substantially removed, and which have a capacity for adsorbed water of not greater than 10, and preferably not greater than 6, weight percent when measured at 25° C. and a water vapor pressure ($p/p_0$) of 4.6, function in an extraordinary manner with respect to odor elimination. Many of the synthetic zeolites prepared using organic templating agents are readily prepared in a highly siliceous form—some even from reaction mixtures which have no intentionally added aluminum. These zeolites are markedly organophilic and include ZSM-5 (U.S. Pat. No. 3,702,886); ZSM-11 (U.S. Pat. No. 3,709,979); ZSM-35 (U.S. Pat. No. 4,016,245); ZSM-23 (U.S. Pat. No. 4,076,842); and ZSM-38 (U.S. Pat. No. 4,046,859) to name only a few. According to these authors, the silica molecular sieves known as silicalite and F-silicalite are particularly suitable for use as odor-controlling agents. These materials are disclosed in U.S. Pat. Nos. 4,061,724 and 4,073,865, respectively. To the extent the aforesaid siliceous sieves are synthesized to have $SiO_2/AlO_2$ ratios greater than 35, they are frequently suitable for use in the present articles without any additional treatment to increase their degree of hydrophobicity. Molecular sieves which cannot be directly synthesized to have both the desired high Si/Al and/or degree of hydrophobicity ratios can be subjected to dealumination techniques, fluorine treatments and the like, which result in organophilic zeolite products. High-temperature steaming procedures for treating zeolite Y which result in hydrophobic product forms are reported by P. K. Maher et al, "Molecular Sieve Zeolites", Advan. Chem. Ser. 101, American Chemical Society, Washington, D.C., 1971, p. 266. A more recently reported procedure applicable to the manufacture of "high" zeolite species generally, involves dealumination and the substitution of silicon into the dealuminated lattice site. This process is disclosed in U.S. Pat. No. 4,503,023 issued Mar. 5, 1985 to Skeels et al. Halogen or halide compound treatments for zeolites to increase their hydrophobicity are disclosed in U.S. Pat. Nos. 4,569,833 and 4,297,335. Steam-treated zeolite Y, prepared per U.S. Pat. No. 4,331,694, and denominated "LZ-10", is a particularly useful odor-controlling agent.

Various other modified zeolite-type materials, such as the manganese-aluminum-phosphorus-silicon-oxide molecular sieves described in U.S. Pat. No. 4,793,833, Lok et al, assigned to UOP, can be used herein. See also U.S. Pat. Nos. 4,604,110; 4,437,429; and 4,648,977, for other zeolitic odor-controlling compositions.

Mixtures of zeolites, especially mixtures of the aforementioned "intermediate" and "high" $SiO_2/AlO_2$ zeolites, can also be used in the practice of this invention, according to the desires of the formulator.

II. Absorbent Gelling Material—As is well-known from recent commercial practice, absorbent gelling materials (sometimes referred to as "super-sorbers") are becoming broadly used in absorbent articles. In general, such AGM's have been used only for their, fluid-absorbing properties. Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those which, upon contact with fluids (i.e., liquids) such as water or body fluids, imbibe such fluids and thereby form hydrogels. In this manner, fluid discharged into the absorbent structures herein can be acquired and held. These preferred absorbent gelling materials will generally comprise substantially, water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the absorbent gelling materials used herein.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization." Typically, commercial absorbent gelling materials have a degree of neutralization somewhat less than 90%.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1-0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issued Mar. 31, 1987, Reissue 32,649. The absorbent gelling materials which are especially useful in the absorbent articles herein are those which have an equilibrium extractables content in synthetic urine of no more than about 17%, preferably no more than about 10% by weight of the absorbent gelling material.

The absorbent gelling materials hereinbefore described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use herein are absorbent gelling material particles substantially all of which have a particle size of from about 30 microns to about 2 mm. "Particle Size" as used herein means the weighted average of the smallest dimension of the individual particles.

The amount of absorbent gelling material particles used in absorbent cores will depend upon the degree of absorbent capacity desired, and will generally comprise from about 2% to 50% by weight of the absorbent core, more typically from about 5% to 20% by weight of the absorbent core.

When absorbent gelling material particles are to be used in the cores of the absorbent articles herein, such cores can be prepared by any process or technique which provides a web comprising a combination of the fibers and the gelling material particles. For example, web cores can be formed by air-laying a substantially dry mixture of hydrophilic fibers and absorbent gelling material particles and, if desired or necessary, by densifying the resulting web. Such a procedure is described more fully in Weisman and Goldman; U.S. Pat. No. 4,610,678; Issued Sep. 9, 1986. As indicated in this U.S. Pat. No. 4,610,678, the air-laid webs formed by such a procedure will preferably comprise substantially unbonded fibers and will preferably have a moisture content of 10% or less.

The density of the absorbent cores which comprise webs of hydrophilic fibers and absorbent gelling material particles can be of importance in determining the absorbent properties of the cores and of the absorbent articles in which such cores are employed. The density of such absorbent cores herein will preferably be in the range of from about 0.06 to about 0.3 g/cm$^3$, and more preferably within the range of from about 0.09 to about 0.22 g/cm$^3$. Typically the basis weight of the absorbent cores herein can range from about 0.02 to 0.12 g/cm$^2$.

Density values for cores of this type can be calculated from basis weight and caliper. Caliper is measured under a confining pressure of 0.137 psi (0.94 kPa). Density and basis weight values include the weight of the absorbent gelling materials and the odor-control material. Density of the cores herein need not be uniform throughout the core. Within the density ranges hereinbefore set forth, the cores can contain regions or zones of relatively higher or relatively lower density.

III. Binders—The binder materials employed in the practice of this invention are conventional materials well-known in commerce under various trade names such as GELFOAM, PURAGEL, LAVERAL, MALTRIN and METHOCEL, said trade names being mentioned here by way of example, and not by way of limitation. In general, the binders herein are soluble or dispersible in water or body fluids such as blood, urine, and the like. Chemically, such binder materials comprise various starch, cellulose, modified starch, modified cellulose, gum acacia/gum arabic, soluble gelatin, etc. materials. Methylcellulose (e.g., METHOCEL A15-LV) and hydroxypropylcellulose (e.g., METHO- CEL 5E) are typical of the preferred bind used herein. Typically, the binder will comprise at least about 1%, preferably 3%-20%, by weight of the final particles or aggregates produced herein. In general, about 6% (wt.) of the binder is sufficient to provide the desired high loading levels of zeolite with the AGM, without substantially interfering with the properties of either the zeolite or the AGM, yet with the production of a final product which is substantially nondusting under ordinary handling conditions. A process for using the binders to prepare the particles of this invention is described hereinafter. Similar procedures can be used to prepare aggregates, using AGM "fines", which can be a substantial economic advantage.

IV. Additional Absorbents—Typically, finished absorbent articles will contain additional fibrous absorbent material such as cotton fluff, cellulose pulp, chemi-thermomechanical pulp, and the like, well-known in commercial practice.

V. Front-Face Material—The finished articles herein will typically be provided with a fluid-receiving facing material. The front-face (or, "topsheet") material used herein is preferably a "nonstaining" hydrophobic, fluid-permeable sheet. Hydrophobic sheet materials of the type typically employed in the practice of this invention can be prepared by methods well-described in the patent literature. For example, according to the process of U.S. Pat. No. 4,324,246, Mullane and Smith, Apr. 13, 1982, a sample of thermoplastic material such as 0.0038 cm thick polyethylene film is heated above its softening point. (The softening point is the temperature at which the thermoplastic material can be formed or molded and is less than the melting point of the material.) The heated thermoplastic material in sheet form is then brought into contact with a heated forming screen. The forming screen is preferably an apertured wire mesh screen having the desired aperture size, pattern and configuration. A vacuum i s used to draw the heated film against the forming screen, thereby forming the film into the desired pattern and having the desired hole sizes. While the vacuum is still being applied to the film, a jet of hot air is passed over the film. The hot air jet perforates the film in a pattern corresponding to the pattern and size of apertures in the forming screen.

Fluid-permeable sheets prepared in the manner of the Mullane et al patent are conveniently referred to as "formed films". The caliper of such films is important since, if the caliper is too great, liquid may accumulate in the apertures and not readily pass therethrough. For the manufacture of absorbent articles such as diapers, catamenials, incontinence articles, and the like, the sheets typically have a caliper of less than about 0.075 cm, or preferably less than about 0.064 cm.

Another formed-film sheet material useful herein is the resilient, 3-dimensional web exhibiting a fiber-like appearance and tactile impression, comprising a fluid-impervious plastic material, with said web having a multiplicity of apertures, the apertures being defined by a multiplicity of intersecting fiberlike elements, all as disclosed in U.S. Pat. No. 4,342,314, Radel and Thompson, Aug. 3, 1982. The Radel and Thompson sheet materials can be prepared using hydrophobic plastics such as polyethylene, polypropylene, PVC, and the like, and are well-known for use in absorbent products such as catamenials, and the like.

Yet another type of sheet material useful herein is described in U.S. Pat. No. 3,929,135, Thompson, Dec. 30, 1975, and consists of hydrophobic polymer films having holes which are in the form of tapered capillaries. These "tapered capillary" sheets are also known for use in absorbent articles, including adult incontinence articles. They may be prepared from various hydrophobic polymers, as mentioned hereinabove; typically, low density polyethylene having thickness of from 0.0025 to 0.0051 cm is employed.

Reference to U.S. Pat. No. 3,929,135 can be made in order to further visualize tapered capillary sheets. In use, the apices of the capillaries in such tapered capillary topsheets are in contact with the underlying absorbent core material. Generally, tapered capillaries are in the form of a frustrum of a conical surface, but it is to be understood that any generally tapered structure, such as a frustrum of a pyramid or the like with a triangular, square, or polygonal base, is within the term "tapered capillary"; circular tapered capillaries, however, are used in this description for convenience. It is also to be understood that the tapered capillaries can be asymmetric (i.e., the angle of taper on one side can be different from that on another side) and that the angle of taper can change continuously (i.e., be curved) over the distance from base to apex. In the latter case, the angle of taper is defined as the angle of the tangent to the side of the capillary at its point of minimum apex opening dimension. The angle of taper suitable for use in topsheets according to the practice of this invention is from about 10° to about 60°.

Base opening dimension of the capillaries is defined as the maximum open measurement in the plane of topsheet at said tapered capillary. Apex opening dimension is defined as the maximum open measurement in the apex of said tapered capillary, which apex is remote from the plane of the topsheet. When the tapered capillary is in the form of a frustrum of a conical surface, the base and apex opening dimensions are, respectively, the base diameter and the apex diameter. Base diameter and apex diameter are hereinafter used interchangeably with, respectively, base opening dimension and apex opening dimension.

The tapered capillary apex diameter is a diameter which will allow liquid to readily pass from the surface of the topsheet to the underlying absorbent core. The apex diameter is from about 0.004 to about 0.100 inch (0.010 to 0.254 centimeter), preferably from about 0.005 to about 0.020 inch (0.013 to 0.051 centimeter).

The tapered capillary base diameter is selected to satisfy two criteria. The first of these is the subjective feel of the surface of the topsheet which contacts the skin of the user. It has been discovered that polyethylene can be made to exhibit pleasing, clothlike, non-waxy attributes when the base diameter is within the range from about 0.006 to about 0.250 inch (0.015 to 0.635 centimeter). Preferably, the base diameter should be within the range of from about 0.030 to about 0.060 inch (0.076 to 0.152 centimeter). The second criterion is that the capillary base diameter be small enough to allow an expected liquid droplet to bridge across at least one capillary. This criterion is satisfied by the above dimensions for disposable diapers and sanitary items.

The height of the tapered capillary is defined as the distance between the outermost surface of the topsheet (i.e., that surface which normally contacts the skin of the user) and the apex of the tapered capillary. This height, of course, depends upon apex diameter, base diameter, and angle of taper which have been selected as hereinbefore described. The height of the tapered capillary should provide a structure with a minimum tendency to collapse in use. The characteristics of the material of construction of the topsheet in large measure determine suitable ranges for the height. When the topsheet is low density polyethylene of from 0.001 to 0.002 inch (0.003 to 0.005 cm) thickness and apex diameter and base diameter are in the preferred range, and angle of taper $\alpha$ is in its critical range, the height of the tapered capillary can be from about 0.003 to about 0.159 inch (0.008 to 0.404 centimeter).

A state of relative dryness on the surface of the topsheet implies that most of the liquid which contacts the topsheet is transferred through it to the absorbent element. This in turn implies that each isolated droplet of fluid in contact with the topsheet must be in contact with the base diameter of a tapered capillary. This state of affairs can best be achieved if the land area (the area of the topsheet that exists between the bases of the tapered capillaries) is maintained at a minimum. The minimum limiting value is the case where conical tapered capillaries or pyramidal tapered capillaries are provided in close packed array (where the periphery of the base of each capillary is in contact on all sides with the periphery of the base of adjacent capillaries). The preferred arrangement of minimum land area tends to insure that an individual droplet will contact at least one tapered capillary. A preferred arrangement in disposable diapers is where the tapered capillaries as hereinbefore described are in ordered arrangement with from about 30 to about 1500 tapered capillaries per square inch of topsheet (5 to 231 per square centimeter).

Tapered capillary sheets can be manufactured in any of several ways well known in the art. One particularly suitable method is to provide a heated mold with male elements of the shape and arrangement of the desired tapered capillaries (hereinafter a pin mold). Each male element is secured in such a fashion that its apex extends away from the base of the pin mold. A portion of sheet material is brought into contact with the heated pin mold between the mold and a resilient backing plate. Pressure is applied to the combination of mold, sheet and resilient back plate and tapered capillaries are formed in the sheet to make the tapered capillary topsheet. An alternate way of constructing the topsheet is to subject a portion of liquid-impervious material to vacuum forming over an appropriate mold. After forming tapered capillary sheets in one of the aforementioned ways, it may be necessary to physically remove material from the apices of the capillaries so as to insure that the apex diameters are the desired value. Such removal of material can be accomplished by, for example, subjecting the apices to controlled abrasion or by heating the formed topsheet so as to melt open the apices. See, also, U.S. Pat. No. 4,629,643, Curro and Linman, Dec. 16, 1986, for a microapertured polymeric film with improved tactile impression, which can also be used in the practice of this invention.

A highly-preferred fluid-permeable formed-film sheet material which can be employed in the practice of this invention is disclosed in U.S. Pat. No. 4,463,045, Ahr et al, Jul. 31, 1984, and reference can be made to that patent to further assist visualization of the Ahr et al structures.

In general terms, the sheets provided by U.S. Pat. No. 4,463,045 are designed not only to provide a desirable cloth-like tactile impression, but also to substantially eliminate surface gloss. Thus, sheets made of plastic do not have an undesirably shiny, "plasticky" appearance.

Such highly-preferred sheet materials can be succinctly described as being a macroscopically expanded three-dimensional plastic "web" having at least one visible surface which appears substantially nonglossy when exposed to light, substantially all of said visible surface exhibiting a regularly spaced, microscopic pattern of discrete surface aberrations, each of said surface aberrations having its amplitude oriented perpendicular to the surface in which said surface aberration originates, each of said surface aberrations having a maximum dimension of less than about 6 mils, as measured in a plane oriented substantially perpendicular to its amplitude, whereby said surface aberrations are not discernible to the normal naked eye when the perpendicular distance between the viewer's eye and the plane of said web is at least about 12 inches, each of said surface aberrations also being free of planar areas which are large enough to inscribe a 4 mil diameter circle and so spaced relative to all adjacent surface aberrations that the maximum diameter of any circle which can be inscribed on any planar surface intermediate said surface aberration and said adjacent surface aberrations on any portion of said visible surface is less than about 4 mils, whereby any light incident upon any portion of said visible surface is diffusely reflected into a multiplicity of directions by said surface aberrations so that said visible surface appears substantially nonglossy.

The '045 sheet materials can have at least a portion of said surface aberrations comprising protuberances projecting generally outwardly from the surface, and can have at least a portion of said surface aberrations comprising depressions projecting generally inwardly from the surface of said web.

The manufacture of these preferred sheets can be achieved by use of a forming screen or structure, as generally noted hereinabove, which provides said surface aberrations by virtue of "knuckles" on the support member. (The preparation of such sheets is described in great detail in U.S. Pat. No. 4,463,045, and their method of preparation forms no part of this invention.) In general, the resulting surface aberrations correspond to the knuckles of a woven mesh support structure which directly contacts the visible surface of said plastic sheet during production thereof.

In a preferred manufacturing method, the woven mesh support structure which directly contacts the visible surface of said sheet is comprised of filaments having a diameter between about one and about two mils and a mesh count between about 160 filaments per lineal inch (2.54 cms) by 160 filaments per lineal inch (2.54 cms) and about 400 filaments per lineal inch (2.54 cms) by 400 filaments per lineal inch (2.54 cms).

Preferred sheets herein are those wherein said surface aberrations have an average amplitude of at least about 0.2 mils, more preferably at least about 0.3 mils. Most preferably, sheets having an amplitude of each of said surface aberrations, as measured perpendicular to the surface in which said surface aberration originates, within the range of about ±20%, desirably ±10%, of the average value of the amplitude for all adjacent surface aberrations are used.

"One-way" sheets whose back faces are treated with hydrophilic latex are described in U.S. Pat. No. 4,735,843, Noda, Apr. 5, 1988, and these can also be employed herein.

In addition to the sophisticated apertured materials mentioned hereinabove, the practice of the present invention may also be undertaken with hydrophobic sheet materials having simple holes punched therethrough.

It will be understood from the foregoing that the aforesaid, preferred, "sheet" or "film" materials used in the practice of this invention are substantially different from fibrous nonwoven materials, which are characterized by a large number of fibers which overlap each other throughout the thickness of the material. Moreover, such sheet materials are made from materials (preferably, hydrophobic thermoplastic polymeric materials) which provide a clean-appearing, stain-resistant or "non-staining" surface, in use.

Other topsheet materials which can be used herein include, for example, various nonabsorbent fibrous or filamentous network sheets which are aqueous-fluid-permeable by virtue of a multiplicity of holes or channels passing therethrough. Such sheet materials can be prepared by methods well-described in the patent literature. For example, according to the process of U.S. Pat. No. 4,636,419, Madsen et al, Jan. 13, 1987, sheets comprising a network of ribboned filaments of two dissimilar chemical types, and with two dissimilar melting or softening points, are contacted and cooled to allow the formation of a network sheet characterized by said different transverse and longitudinal polymer materials. Such sheets can be used in the practice of this invention.

Another sheet material useful herein is the formaminous net comprising a reticular network of polymeric filaments, said net comprising two arrays of filaments oriented at a displacement angle of 20–90 degrees. Reference can be made to European Patent Application 0215417, filed Jun. 9, 1986, Sneyd et al, to further assist visualization of this sheet. The aforesaid sheet materials can be prepared using hydrophobic plastics such as polyethylene, polypropylene, PVC, and the like, and are well-known for use in absorbent products such as catamenials, and the like. Such sheet materials typically have a basis weight of 0.5–5.0 ounces/yd$^2$ (0.0016 g/cm$^2$–0.016 g/cm$^2$), a caliper of 5-25 mils, an open area of 30–80% and a mesh of 20–40. Conventional nonwoven topsheets can also be employed.

VI. Backing Sheet—The backing sheet is conventional, and can comprise a fluid-impervious polymer sheet, for example polyethylene or polypropylene, that is thin enough to be flexible. A polyethylene sheet 0.001–0.5 mm thick is typical. Flushable or biodegradable backing sheets can also be used, e.g., with pantiliner devices herein.

VII. Optional Retaining Means—The absorbent structures herein can optionally, but preferably, be provided with means to hold them in place on or near the user's body to allow the structures to perform their intended function. For example, diapers and incontinence garments can be provided with well-known commercially-available tape fasteners. Sanitary napkins can be provided with glue stripes facing outward on their backsheet in well-known fashion. Various pins, clips and fasteners of well-known types can optionally be employed.

VIII. Optional Adjunct Odor-Controlling Materials—The compositions and articles of this invention can also contain an effective, i.e., odor-controlling, amount of various additional non-zeolite odor-controlling materials to further expand their capacity for controlling odors, as well as the range of odor types being controlled. Such materials include, for example, activated carbon, kieselguhr, cetyl pyridinium chloride, zinc chloride, copper salts, copper ions, and the like. Such materials typically comprise 0.01% to 15% of the compositions herein. Stated otherwise, materials such as activated carbon can typically be present at the 0.1 g to 5.0 g level in absorbent articles of the type disclosed herein to provide additional odor control benefits.

IX. Preparation of AGM/Zeolitic/Binder Particles—A simple, yet effective, method for preparing the particles herein employs a fluidized bed coating apparatus, as described more fully in Example I. However, it will be appreciated that other types of coating apparatus, agglomerators, or the like, can also be used to prepare such particles.

EXAMPLE I 100 g of METHOCEL 5E (binder) are dissolved in 1900 ml deionized water. Zeolite (ABSCENTS powder; 398 g) is added to the METHOCEL solution (19.9% dispersion). A high shear mixer (Tekmar High Shear Mixer Model SD45) is used to create a dispersion of the zeolite. Typical shear time 15 minutes.

498 g. of commercial AGM granules (polyacrylate) are placed in a Worster Fluid Bed Coater (ca. 10 cm Ascoat Unit Model 101, Lasko Co., Leominster, Mass.). The AGM material is fluidized in the bed at an air flow of 18 scfm (standard ft$^2$/min); the inlet temperature is brought to 138° F. (58.9° C.).

The flow of ABSCENTS/METHOCEL coating solution into the spray nozzle is begun (¼-Round Spray Nozzle made by The Spraying Systems Co.; 0.40/0.100 fluid cap.; 0.120 air cap.). The flow rate is set at 7.7 g/min. Exit air temperature is 77°–84° F. (25° to 28.9° C.). At these operating conditions, a run takes about 5 hours to complete.

In typical runs, particles prepared in the foregoing manner can comprise 40 to 60% (wt.) AGM; 10 to 40% (wt.) zeolite, the balance comprising the binder (generally 6%–10% wt.). Particle sizes range from 100 to 700 microns.

EXAMPLE II

Following the procedure of Example I , a composition comprising 62% starch acrylate (SANWET), 38% zeolite (CBV400) and binder (hydroxypropyl cellulose) is prepared as particles in the 300–500 micron size range.

EXAMPLE III

A mixed odor-controlling agent is in the form of 200–700 micron particles, as follows.

| Ingredient | Percent (wt) |
| --- | --- |
| ABSCENTS (avg. 5 microns) Zeolite | 10 |
| VALFOR CP300-56 Zeolite | 10 |
| Starch Acrylate AGM | 79 |

The composition of Example III is prepared in the manner of Example I, with 1% maltodextrin binder.

EXAMPLE IV

Pads suitable for use as an absorbent structure in diapers, sanitary napkins, and the like comprise a substantially homogeneous blend of the following.

| Ingredient | Percent (wt) |
| --- | --- |
| Kraft Cellulose Fibers (SSK*) | 72 |

-continued

| Ingredient | Percent (wt) |
| --- | --- |
| Zeolite/AGM** | 14 |

*Southern Softwood Kraft.
**Prepared according to Example I.

EXAMPLE V

A lightweight pantiliner suitable for use between menstrual periods, and which can be disposed of in a toilet (i.e., "flushable") comprises a pad (surface area 117 cm$^2$; SSK air felt 3.0 g) containing 1.5 g of the AGM/zeolite particles prepared according to Example II, said pad being interposed between the topsheet of U.S. Pat. No. 4,463,045 and a fibrous, nonwoven, flushable backsheet.

EXAMPLE VI

A catamenial product in the form of a sanitary napkin having two flaps extending outward from its absorbent core is prepared using the pad of Example IV (surface area 117 cm$^2$; 8.5 g SSK air felt), per the design of U.S. Pat. No. 4,687,478, Van Tillburg, Aug. 18, 1987. The nonglossy sheet of U.S. Pat. No. 4,463,045, is used as the topsheet.

EXAMPLE VII

A disposable baby diaper using the odor-control pad of Example IV is prepared as follows. The dimensions listed are for a diaper intended for use with a child in the 6-10 kilogram size range. These dimensions can be modified proportionately for different size children, or for adult incontinence briefs, according to standard practice.
 1. Backsheet: 0.025-0.070 mm polyethylene; width at top and bottom 33 cm; notched inwardly on both sides to a width-at-center of 28.5 cm; length 50.2 cm.
 2. Topsheet: tapered capillary polyethylene topsheet, per U.S. Pat. No. 3,929,135, described hereinabove; width at top and bottom 33 cm; notched inwardly on both sides to a width-at-center of 28.5 cm; length 50.2 cm.
 3. Absorbent core: air-laid wood pulp fibers per Example IV; Taber stiffness range 7-9.5, 8.4 mm thick, calendered; width at top and bottom 28.6 cm; notched inwardly at both sides to a width-at-center of 10.2 cm; length 44.5 cm.
 4. Elastic leg bands: four individual rubber strips (2 per side); width 4.77 mm; length 370 mm; thickness 0.178 mm (all the foregoing dimensions being n the relaxed state).

The diaper of Example VII is prepared in standard fashion by positioning the core-plus-odor control material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic band). This provides a spacing element along each side of the diaper comprising the flexible topsheet/ backsheet material between the inner elastic and the curved edge of the core. The inner bands are glued down along their length in the stretched state. The outer bands are positioned ca. 13 mm from the inner bands, and are glued down along their length in the stretched state. Since the topsheet/backsheet assembly is flexible, the glued-down bands contract to elasticize the sides of the diaper.

It will be understood that the practice of this invention applies not only to human odors, but also to animal odors.

EXAMPLE VIII

A cat litter product comprises the following components.

| Ingredient | Percent (wt.) |
| --- | --- |
| Comminuted Cellulose* | 90 |
| Odor Control Material** | 10 |

*Compacted in granular form.
**AGM particles 750 micron size; 15% wt. ABSCENTS plus 15% wt.

VALFOR 300-68 zeolites (5-10 micron size) adhered to AGM (polyacrylate) particles with METHOCEL.

EXAMPLE IX

Cohesive particles prepared in the manner of Example I comprise 65% acrylate AGM, 20% ABSCENTS, 10% activated carbon and 5% METHOCEL binder.

As can be seen from the foregoing, the compositions of this invention are used in odor-controlling amounts to achieve the desired benefits. This amount can, of course, vary, depending on the intended end-use and severity of the odor. Typically, catamenial products will employ sufficient amounts of said composition to deliver from at least about 0.2 g. to about 0.4 g. of the odor-controlling agent. To assist the formulator, a simple test of odor-controlling capacity of such compositions comprises placing the odor-controlling composition in an absorbent pad of the desired type and uniformly adding a 5 ml. aliquot of a defined onion/ ammonia odor medium (20 g. commercial onion powder, 900 mls H$_2$O containing 7.5 g. NaHPO$_4$.7H$_2$O, 4.5 g. K$_2$SO$_4$, 1.8 g. MgCl$_2$.6H$_2$O, 3.0 g NaCl, 15.0 g. urea; 10.0 ml of 1 normal HCl; stirred 4 hours, filtered, NH$_4$OH and H$_2$O added to yield NH$_4$OH concentration 500-1500 ppm, as desired). After equilibrating for 1 hour in a closed container with a sniff port, the odor-controlling capacity of the composition can be judged and the amounts used can be adjusted accordingly.

What is claimed is:

1. An absorbent structure in the form of a diaper, catamenial or pantiliner, comprising a cohesive mixture in the form of particles or aggregates, said particles or aggregates having a size, by sieve analysis, greater than about 100 microns, said particles comprising:
 (a) at least 20% by weight of a particulate odor-controlling agent which is a mixture of zeolite and activated carbon odor-controlling agents;
 (b) at least 40% by weight of an absorbent gelling material; and
 (c) a water-soluble or water-dispersible binder material which is a member selected from the group consisting of hydroxypropyl celluloses, hydroxyethyl celluloses, hydroxymethyl celluloses, C$_1$-C$_3$ alkyl-substituted cellulose, maltodextrin, and mixtures thereof.

* * * * *